(12) United States Patent
Banin et al.

(10) Patent No.: US 7,528,947 B2
(45) Date of Patent: May 5, 2009

(54) NANOPARTICLES FUNCTIONALIZED PROBES AND METHODS FOR PREPARING SUCH PROBES

(75) Inventors: Uri Banin, Mevasseret Zion (IL); Taleb Mokari, Jerusalem (IL); Yuval Ebenstein, Yavne (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 59 days.

(21) Appl. No.: 10/564,036

(22) PCT Filed: Jul. 8, 2004

(86) PCT No.: PCT/IL2004/000613

§ 371 (c)(1),
(2), (4) Date: Aug. 4, 2006

(87) PCT Pub. No.: WO2005/006347

PCT Pub. Date: Jan. 20, 2005

(65) Prior Publication Data

US 2007/0035724 A1    Feb. 15, 2007

Related U.S. Application Data

(60) Provisional application No. 60/485,731, filed on Jul. 10, 2003.

(51) Int. Cl.
*G01J 3/44* (2006.01)

(52) U.S. Cl. .................... 356/301; 356/317

(58) Field of Classification Search ............ 356/301, 356/317
See application file for complete search history.

(56) References Cited

U.S. PATENT DOCUMENTS

| | | | | |
|---|---|---|---|---|
| 6,002,471 A | * | 12/1999 | Quake | 356/301 |
| 6,487,326 B1 | * | 11/2002 | Pantano et al. | 436/172 |
| 6,850,323 B2 | * | 2/2005 | Anderson | 356/301 |

FOREIGN PATENT DOCUMENTS

| | | |
|---|---|---|
| WO | WO 02/25745 A2 | 3/2002 |
| WO | WO 03/097904 A1 | 11/2003 |

OTHER PUBLICATIONS

Kopelman, R. et al. "Nanometer Light Source and Molecular Exciton Microscopy"; Journal of Luminescence 45; 1990, pp. 298-299, North Holland.

Sekatski, S.K. et al. "Nanometer-resolution scanning optical microscope with resonance excitation of the fluorescence of the samples from a single-atom excited center"; JETP Lett., vol. 63, No. 5, pp. 319-323, Mar. 10, 1999.

(Continued)

*Primary Examiner*—Kara E Geisel
(74) *Attorney, Agent, or Firm*—Browdy and Neimark, P.L.L.C.

(57) ABSTRACT

The present invention provides probes functionalized with nanoparticles, methods for binding nanoparticles to the probes and the use of such probes in nanometer scale imaging techniques. More specifically, the present invention provides a tip device having at least a portion thereof with an outer surface bound to at least one sub-layer of a material comprising nanoparticles, the nanoparticles acting as donors, acceptors, modifiers, quenchers and/or enhancers with respect to electromagnetic radiation.

34 Claims, 7 Drawing Sheets

OTHER PUBLICATIONS

Forster, T. "Delocalized Excitation and Excitation Transfer"; Modern Quantum Chemistry; Academic; pp. 93-137; 1965, New York.

Weiss, S. "Fluorescence Spectroscopy of Single Biomolecules"; Science; vol. 283, pp. 1676-1683; Mar. 12, 1999.

Deniz, A.A. et al. Single-molecule protein folding: Diffusion fluorescence resonance energy transfer studies Of the denaturation of chymotrypsin inhibitor 2; PNAS; vol. 97, No. 10 pp. 5197-5184, May 9, 2000.

Shubeitta, G.T. et al. "Local fluorescent probes for the fluorescence resonance energy transfer scanning Near-field optical microscopy"; Applied Physics Letters; vol. 80, No. 15, pp. 2625-2627, 2002.

Kan, S et al. "Synthesis and size-dependent properties of zinc-blende semiconductor quantum rods"; Nature Materials; vol. 2, pp. 72, 155-158, Mar. 2003.

Dubertret, B et al. "In Vivo Imaging of Quantum Dots Encapsulated in Phospholipid Micelles"; Science, vol. 298, pp. 1759-1762, Nov. 29, 2002.

Willard, D.M. et al. "CdSe-ZnS Quantum Dots as Resonance Energy Transfer Donors in a Model Protein-Protein Binding Assay"; Nano Letters; vol. 1, No. 9, pp. 469-474, 2001.

Shubeita, G.T. et al. Scanning near-field optical microscopy using semiconductor nanocrystals as a local Fluorescence and fluorescence resonance energy transfer source; Journal of Microscopy. vol. 210, pp. 274-278, 2003.

Murray, C.B. et al. "Synthesis and Characterization of Nearly Monidisperse CdE (E=S, Se, Te) Semiconductor Nanocrystallites"; J. AM. Chem. Soc, vol. 115, pp. 8706-8715; 1993.

Mokari, T. et al. "Synthesis and Properties of CdSe/ZnS Core/Shell Nanorods"; Chem. Mater, vol. 15, pp. 3955-3960, 2003.

Cao, Y et al. "Growth and Properties of Semiconductor Core/Shell Nanocrystals with InAs Cores"; J. AM. Chem. Soc, vol. 122, pp. 9692-9702, 2000.

Anderson, M. "Locally enhanced Raman spectroscopy with an atomic force microscope"; Applied Physics Letters, vol. 76, No. 21, pp. 3130-3132, May 22, 2000.

Vickery, S.A. et al. "Combining AFM and FRET for high resolution fluorescence microscopy"; Journal of Microscopy, vol. 202, pp. 408-412, May 2001.

Okamoto, T. et al. "Near-Field scanning Optical Microscope Using a Gold Particle"; J. Appl. Phys. vol. 36, XP-000732147, pp. L166-L169, 1997.

Wessel, J. "Surface-enhanced optical microscopy"; J. Opt. Soc. AM. B/vol. 2, No. 9, XP-002300715, Sep. 1985.

* cited by examiner

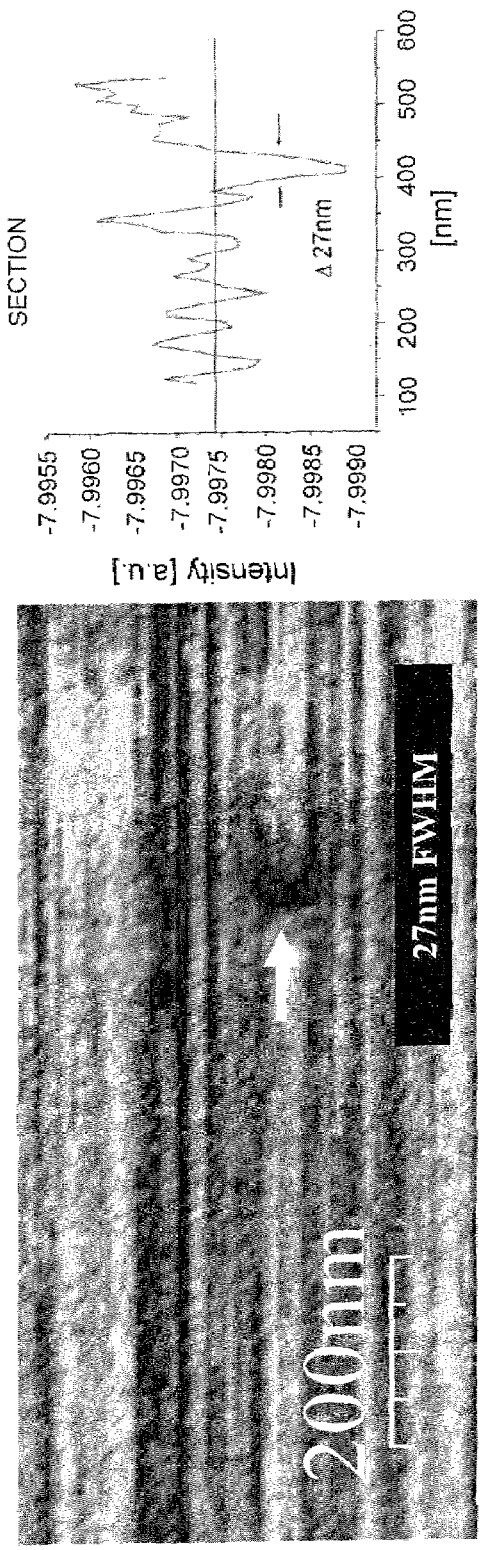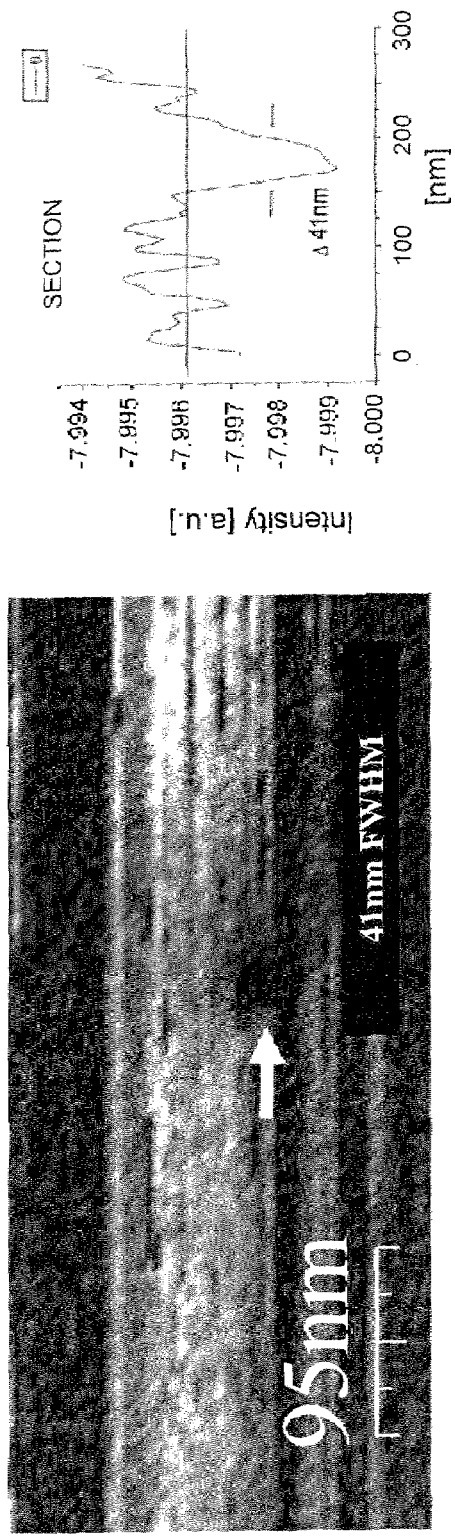
FIG. 7A
FIG. 7B

NANOPARTICLES FUNCTIONALIZED PROBES AND METHODS FOR PREPARING SUCH PROBES

FIELD OF THE INVENTION

The invention is generally in the field of nanomaterials and relates to a nanoparticles functionalized probe and method for preparation thereof. The probe of the present invention is particularly useful in high resolution imaging.

LIST OF REFERENCES

The following references are considered to be pertinent for the purpose of understanding the background of the present invention:
1. Kopelman, R.; Lewis, A.; Lieberman, K. *J. Lumin.* 1990, 45, 298.
2. Sekatskii, S. K.; Letokhov, V. S. *JETP Lett.* 1996, 63, 319.
3. Forster, T. *Modern Quantum Chemistry*; Academic, New York; 1965.
4. S. Weiss, *Science,* 1999, 283, 1676.
5. Deniz, A. A. et al, *Proc. Natl. Acad. Sci. USA.* 2000, 97, 5179.
6. Shubeita, G. T. et al, *Appl. Plays. Lett.* 2002, 80, 2625.
7. Kan, S. et al, *Nature Mater.,* 2003, 2, 155.
8. Dubertret, B. et al, *Science* 2002, 298, 1759.
9. Willard, D. M. et al, *Nano Lett.* 2001, 1, 469.
10. Shubeita, G. T. et al, *J. Microsc.* 2003, 210, 274.
11. Murray C. B. et al, *J. Am. Chem. Soc.* 1993, 115, 8706.
12. WO 02/25745
13. WO 03/097904
14. T. Mokari, U. Banin, *Chem. Mater.* 2003, 15, 3955.
15. Cao Y. W.; Banin, U. *J. Am. Chem. Soc.* 2000, 122, 9692.
16. Anderson, M. S. *Appl Phys. Lett.* 2000, 76, 3130.

The above references will be acknowledged in the text below by indicating their numbers [in brackets] from the above list.

BACKGROUND OF THE INVENTION

High resolution optical imaging is an important tool in many fields of physical science, and especially in biology and medicine. Far field optical microscopy techniques are used extensively for imaging biological samples with diffraction limited resolution of ~300 nm. Near field applications, such as optical data storage, inspection, microscopy, allows imaging with resolution below the optical diffraction limit by generating a point-like light source of sub-wavelength dimensions nearby the sample surface. This is typically achieved either by defining small apertures on opaque screens, or by passing the light through point-like tips of sub-wavelength dimensions. The tips (constituting point-like light sources) are located in close proximity of the object (the sample surface) in order to provide high optical resolution of the scanning system in the near field.

Near field scanning optical systems often utilize the methods employed in widely spread scanning probe microscopy (SPM) techniques. Among these techniques, scanning tunneling microscopy (STM) for studying conductive surfaces and atomic force microscopy (AFM) for studying also non-conductive surfaces, are the most wide-spread techniques. The AFM methods are of particular relevance and are based on the principle of force sensing between a tip proximal to the sample surface. More specifically, a sharp point is fixed to the end of a spring-like cantilever and is brought so close to the surface that the forces between the tip and the surface deflect the cantilever. This deflection is detected most commonly by means of sensing the position of a light beam reflected from the cantilever onto a split photodiode detector. In one common AFM mode, contact mode, the measured deflection is translated into a correction signal that is used as feedback to keep the deflection constant by moving the cantilever up or down and thus reflecting the sample surface topography. Other methods are known for AFM including tapping mode AFM and conductive AFM.

The resolution of near field scanning optical microscopy (NSOM) obtainable with conventional tapered fiber probes is typically on the order of 100 nm. It is difficult to improve the resolution of this technique to the molecular level due to the finite skin depth of the metal coating surrounding the fiber probe, and its low throughput and low damage threshold. This limitation can be overcome by implementing apertureless-NSOM techniques. The contrast mechanism of these methods is based on detecting near field effects, locally induced by a sharp probe proximal to the sample. With the increasingly wide-spread and robust implementation of AFM (atomic force microscopy) schemes briefly described above, the aperturelss-NSOM techniques also become more accessible.

One approach to enhance optical resolution via apertureless-NSOM is the exploitation of strongly distance dependant physical interactions such as FRET (fluorescence resonance energy transfer) [1,2]. FRET is widely used in solution experiments and in single molecule spectroscopy, to determine molecular scale distances in biological samples. The intensity of the FRET signal scales as the inverse sixth power of the distance between donor and acceptor molecules [3]. The range of the FRET process can be estimated from $R_0$, the distance where the interaction is at 50% efficiency, with typical values of 1-10 nm. During the FRET process, energy is transferred non-radiatively through a dipole-dipole interaction from the excited donor chromophore, to the acceptor which fluoresces. Detection of the relative intensities of donor and acceptor fluorescence provides information regarding their relative distance and orientation [4, 5]. This high sensitivity of FRET to molecular scale distances has been suggested as a contrast mechanism for high resolution optical imaging [2].

FRET based microscopy schemes are realized by the immobilization of donor or acceptor chromophores on the tip of a scanning probe microscope used to image the complimentary FRET species on the substrate. As the functionalized tip approaches a chromophore on the substrate, the FRET interaction leads to donor quenching while inducing acceptor emission, indicating the position of the chromophore with potential for molecular-scale resolution.

Several attempts to realize this imaging technique have been reported using pairs of dye molecules. For example, Shubeita et al [6] coated NSOM tips with polymer containing acceptor molecules.

Semiconductor nanocrystals have several advantages over dye molecules as FRET donors. These advantages have also prompted their emerging use as novel biological markers in both in vitro and in in-vivo applications. First, the nanocrystals may be tailored, via control of size, composition and shape [7] to provide exceptional spectral coverage with symmetric emission profiles, enabling optimization of donor-acceptor spectral overlap. Additionally, due to their continuous absorption band they may be excited efficiently at shorter wavelength regions where the acceptor dye molecule has minimal absorption cross section reducing direct acceptor excitation and hence donor-acceptor cross-talk. Finally, as already demonstrated in several applications [8], the nanocrystals are significantly more stable emitters compared to the conventional dye molecules and as mentioned above, this is a critical feature for a feasible FRET microscopy scheme.

Recently, CdSe—ZnS quantum-dots were used as FRET donors in a model protein-protein binding assay demonstrating their advantages for FRET applications [9]. In addition, Shubeita et al [10] have recently used semiconductor nanocrystals to coat NSOM fiber tips. In that case, the fiber tips were dipped in a polymer solution containing the nanocrystals to yield a 30-100 nm thick layer of nanocrystal-stained polymer. The polymer was used to embed the nanoparticles on the fiber tip.

A metal coated AFM tip where the coating was deposited by sputtering was shown by Anderson [16] to yield local enhanced Raman signal.

SUMMARY OF THE INVENTION

The present invention provides scanning probes functionalized with nanoparticles, methods for binding nanoparticles to scanning probes and the use of such probes in nanometer and molecular scale imaging techniques.

Thus, according to a first aspect, the present invention provides a tip device wherein at least a portion thereof has an outer surface bound to a layer of a material comprising nanoparticles, the nanoparticles acting as active media with respect to electromagnetic radiation. Preferably, the tip is configured as a scanning probe microscope (SPM) tip As used herein, the phrase "scanning probe microscope tip" refers to tips used in nanometer scale imaging, including near field scanning optical microscope (NSOM) tips, atomic force microscope (AFM) tips, scanning tunneling microscope (STM) tips, and devices having similar properties. Also, the terms "tip", "tip device" and "probe" are used interchangeably in the present invention and denote a structure having a conical-like geometry, or having a stem-like portion and a head- or apex-like portion, which head- or apex-like portion actually presents the tip itself.

Most preferably, the scanning probe microscope tip is an AFM tip, associated with a cantilever, such that when the tip is brought close to the surface forces occurring between the tip and the surface deflect the cantilever. In an AFM system, the AFM tip is typically scanned across a sample surface to create an image of the detected surface features. Any AFM tip can be used, except for hollow fiber tips such as those disclosed in [10]. Conventional AFM tips are typically made of silicon or $Si_3N_4$. Other possible tips are made of insulator-, semiconductor- or conductor-based materials. Non-limiting examples of such tip materials are glass, diamond, carbon, silicon oxide, titanium oxide, TiN. Often, a conductive layer is used to coat the tip surface. Such layers are typically composed of, Au, Ag, Pt, Al, W, Ti, mixtures thereof such as Cr/Au, Co/Cr, Ti/Pt, Ti/Ni, Pt/Ir and the like.

According to the present invention, the tip comprises at least a portion thereof with an outer surface bound to a layer of a material comprising nanoparticles. The layer of the nanoparticles-containing material has a thickness in a range from sub-monolayer coverage as well as monolayer, multiple layers (up to a thousand layers) or other aggregations that may be suitable or desired on particular applications. The thickness of a particular monolayer is dictated by the size of the nanoparticles that compose it. For example, nanospheres having a diameter of 4 nm will form a monolayer with a thickness of about 5 nm, while particles having a diameter of 8 nm, will form a monolayer with a thickness of about 9 nm.

The nanoparticles are bound to said outer surface of the tip either directly or through a linker molecule, to form a functionalized tip. As used herein the term "bind" or "bound" denotes chemical binding (i.e. chemisorption, covalent linkage or electrostatic linkage) or physical binding (i.e. adsorption).

As indicated above, according to the invention, the nanoparticles provide an active media with respect to electromagnetic radiation. The term "active media" is meant to denote a media capable of interacting with electromagnetic radiation resulting in: 1. absorption of the radiation followed by transfer of the energy to an acceptor or in producing a beam of optical radiation by stimulating electronic, ionic, or molecular transitions to higher energy levels so that when they return to lower energy levels they emit energy or 2. in accepting energy from a donor entity or 3. in enhancing the electromagnetic field locally. Specific examples of such active media are those having spectral properties of donors, acceptors or quenchers. The term "donor" denotes a chemical entity having absorption and emission spectra. Typical donors in the present invention are nanoparticles. The term "acceptor" denotes a chemical entity where a portion of its absorption spectrum is overlapping a portion of the emission spectrum of the donor such that the acceptor is capable of accepting energy from said donor. The term "quencher" denotes a chemical entity capable of accepting energy from another entity such as a molecule in its excited electronic state that would otherwise usually loose its energy by emission of a photon resulting in the quenching of this emission.

Typical acceptor molecules used in the present invention are dye molecules. Non limiting examples of dyes are Rhodamine based dyes, fluoresceines, cyanines, dyomics, alexa fluor dyes, BODIPY (4,4-difluoro-4-bora-3a,4a-diaza-s-indacene) dyes, intercalating dyes, DAPI (4',6-Diamidino-2-phenylindole) dyes and other available dyes. Alternatively, the acceptor molecules are nanoparticles or dye molecules with acceptor spectral properties and the donor molecules are either dye molecules or fluorescent nanocrystals with donor spectral properties (for example InAs acceptors and CdSe donors).

The nanoparticles are made of semiconductor, metal or oxide materials. The nanoparticles are preferably nanocrystals having various shapes such as for example dots, spheres or nearly spheres, rods, tubes, wires or branched structures such as bipods, tripods and tetrapods. Furthermore, the nanoparticles may have the above mentioned shapes in core/shell layered structures. The terms "nanorod", "rod" and "quantum rod" are used interchangeably in the present specification.

Preferably, the nanocrystals are made of a semiconductor material selected from Group II-VI semiconductors, such as for example CdS, CdSe, CdTe, ZnS, ZnSe, ZnO and alloys (e.g. CdZnSe); Group III-V semiconductors such as InAs, tip, GaAs, GaP, InN, GaN, InSb, GaSb and alloys (e.g., InAsP); Group IV-VI semiconductors such as PbSe and PbS and alloys; and Group IV semiconductors such as Si and Ge and alloys.

Additionally, combinations of the above in composite structures consisting of sections with different semiconductor materials, for example CdSe/CdS or any other combinations, as well as core/shell structures of different semiconductors such as for example CdSe/ZnS core/shell nanorods [12], are also within the scope of the present invention.

Alternatively, the nanoparticles are made of metal such as for example gold, silver, platinum, palladium, copper, iron, nickel, titanium, iridium, cobalt, chromium, bismuth, indium and alloys or mixtures such as Co—Cr, Cr—Au, Pt—Ir, Ti—Pt. Metal nanocrystals may be bound, according to the present invention, to AFM tips and proceed as centers for Raman enhancement.

Examples of nanoparticles made of oxide materials are those made of $TiO_2$, $Al_2O_3$, ZnO and the like.

According to another aspect, the present invention provides a method of forming a tip having at least a portion thereof operable as active media with respect to electromagnetic radiation, the method comprising reacting a nanoparticles solution, powder or film with at least a portion of the tip so as to bind a layer of nanoparticles to the outer surface of said at least portion of the tip, the nanoparticles acting as donor, acceptor or quencher with respect to electromagnetic radiation. The term "layer" refers to sub-monolayer coverage as well as monolayer, multiple layers or other aggregations that may be suitable or desired on particular applications.

In a preferred embodiment, the above method comprises providing tip, reacting at least a portion of the tip with linker molecules so as to form a tip having at least a portion thereof bound to the linker molecules, and then reacting the so-obtained tip with a nanoparticles solution to thereby produce the tip having at least a portion thereof operable as active media with respect to electromagnetic radiation. Linker molecules are organic molecules having at least two functional groups, one of the functional groups being capable to react and bind to the tips' surface and another of the functional groups being capable to react and bind to the nanoparticles. Non-limiting examples of suitable functional groups are silane, thiols, carboxylate, amines and the like.

In another preferred embodiment, at least a portion of the tip is preferably silanized with an organosilane compound either in solution or in gas phase to form tip with at least a silanized portion, and the resulting tip is exposed to a solution comprising nanoparticles and a solvent, at temperatures between the solvent freezing point and the solvent boiling point, preferable at room temperature, to form tip having at least a portion thereof with an outer surface bound to a layer of nanoparticles, where the term "layer" refers to sub-mono-layer coverage as well as monolayer, multiple layers or other aggregations that may be suitable or desired on particular applications. The nanoparticles solution is prepared by using solvents or mixtures of solvents capable to bring to the dissolution of nanoparticle powders, for example toluene, chloroform, hexanes, anisole and other organic solvents for hydrophobic coated nanocrystals, and water, alcohols, acetone or other polar solvents for hydrophilic coated and/or surface-charged nanocrystals.

Preferred organosilanes are those bearing a functional group X that may vary widely depending on the desired properties. By way of example and not limitation, X may be COOH, OH, NH(R), $N(R)_2$, $NH_2$, $CF_3$, $OCH_3$, SH, F, Cl, epoxy and COOR, where R represents organic functional groups in general, e.g. hydrocarbon or halocarbons. More specifically, organosilanes used in the present invention are having the formula $X(R_1)_nSi(R_2)_3$, where X is as described above, $R_1$ represents a linear, branched or optionally substituted $C_1$-$C_{10}$ alkylene group, each $R_2$ is independently selected from hydrogen, $C_1$-$C_{10}$ alkyl, $C_1$-$C_{10}$ haloalkyl, hydroxy, $C_1$-$C_{10}$ alkoxy, and n represents one or multiple occurrences of the group $R_1$. Non-limiting examples of organosilanes used in the present invention are aminopropyl triethoxysilane, aminopropylmethyldiethoxysilane, aminoethylaminopropylmethyldimethoxysilane, diethylenediaminopropyl-trimethoxysilane, cyclohexylaminopropyltrimethoxysilane, anilinomethyl-triethoxysilane, methacryloxypropyltriethoxysilane, chloromethyltriethoxysilane, mercaptopropyltrimethoxysilane and the like.

When the tips are made of a metal or coated with a metal such as for example gold, silver, platinum, iridium, cobalt, chromium or alloys or mixtures such as Co—Cr, Cr—Au, Pt—Ir, and Ti—Pt, the bifunctional ligands to be used should have high affinity to metal surfaces. Examples include thiol functionality that binds strongly to gold, silver and platinum surfaces, e.g. dithiols such as hexane-dithiols, aminothiols and the like.

In the case of imaging biological samples in aqueous environment, it is desired to carry out the functionalization of the tips with water-soluble nanoparticles. Such water solubility of the nanocrystals may be achieved by ligand exchange (i.e., by replacing hydrophobic end groups with ligands having hydrophilic end groups such as acetic or amine groups), or by suitable hydrophilic polymer coating, or by silanization of the nanocrystal surfaces, or by peptide coating or other means.

In another aspect, the present invention provides an optical apparatus for use in analyzing a sample, the apparatus comprising at least one tip configured as described above.

In a further aspect, the present invention provides a method for use in imaging a sample by exciting the sample with electromagnetic radiation and following the emitted light produced as a result of interaction between donor-acceptor pair formed by the above-described tip and the sample.

The functionalized tips prepared by the method of the present invention remain sharp, retaining the benefits of AFM imaging, while possessing the photophysical properties of the attached nanocrystals. Emitting probes with various emission colors can be prepared and easily tailored for specific applications, such as FRET based microscopy, locally enhanced Raman based microscopy, locally enhanced second harmonic generation microscopy, locally enhanced non-linear optical microscopy and chemical force microscopy. In case of FRET schemes for example, where the nanocrystals on the tip serve either as FRET donors or acceptors interacting with chromophores on the scanned sample, a contrast mechanism for high resolution optical imaging in the near field is provided.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 7A, 7B—two scans showing fluorescence quenching for InAs functionalized tip over a CdSe nanocrystal.

DETAILED DESCRIPTION OF THE INVENTION

The present invention provides a tip device functionalized with nanoparticles, methods for binding nanoparticles to the tip device and the use of the tips in nanometer scale imaging techniques. In case of FRET techniques, the nanoparticles on the tip serve as an active medium with respect to electromagnetic radiation, such as FRET donors or acceptors interacting with chromophores on a sample with which the tip is associated.

Figure 1:
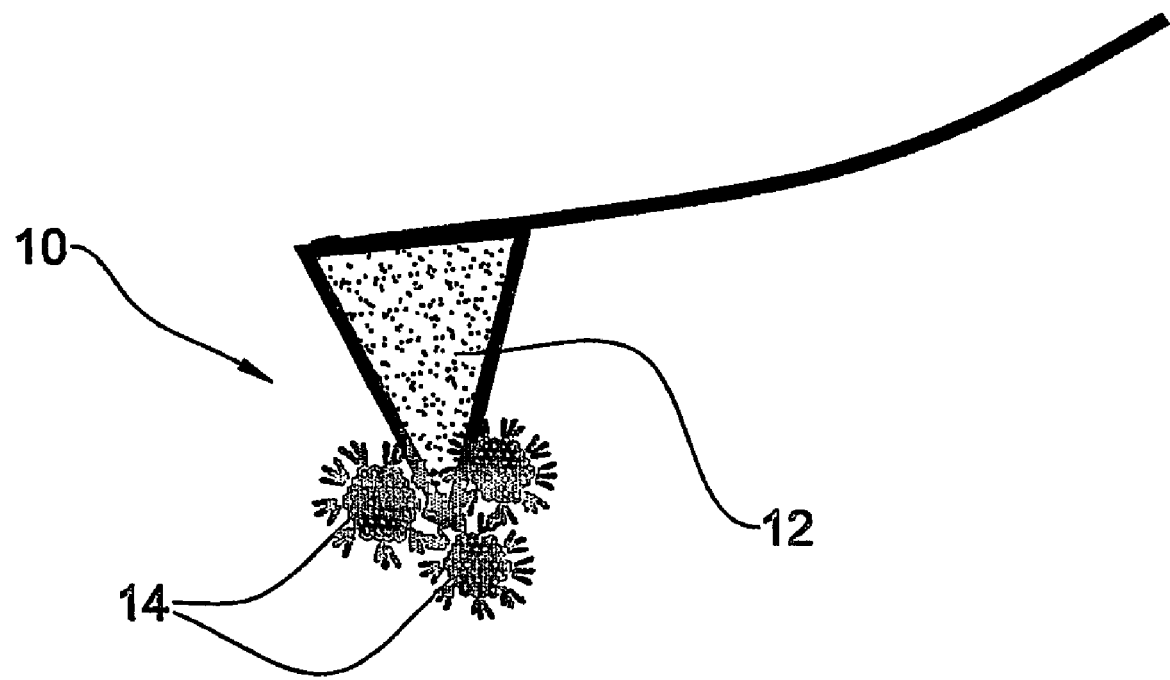
FIG. 1 is a schematic representation of a tip device functionalized by semiconductor nanocrystals according to the invention.

FRET based microscopy schemes are realized by the immobilization of donor or acceptor chromophores on the tip of a scanning probe microscope used to image the complimentary FRET species on the substrate as seen schematically in FIG. 1. A tip device 10 is a conically shaped structure, which according to the invention has at least a distal portion (or top) 12 thereof formed with bound nanoparticles 14. This nanoparticles-bound portion 12 serves as the active medium with respect to electromagnetic radiation. In an optional embodiment, the nanoparticles 14 are bound to the portion 12 through linker molecules which are organic molecules having at least two functional groups. One of the functional groups is capable to react and bind to the tips' surface and another of the functional groups is capable to react and bind to the nanoparticles.

Figure 8A:
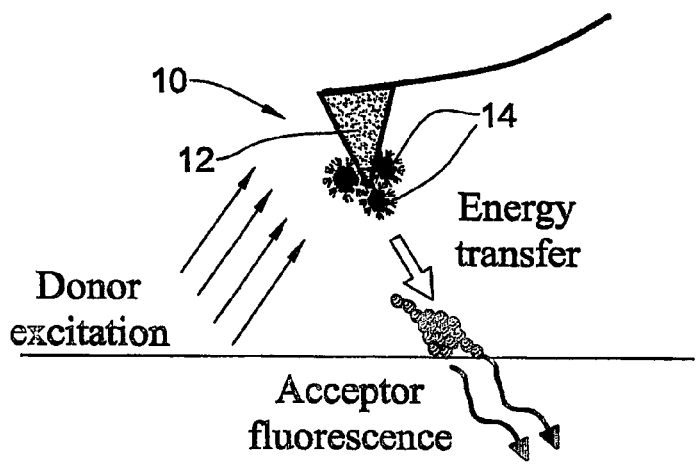
FIG. 8A—is a schematic representation of a tip device functionalized by semiconductor nanocrystals according to the invention and the use of this tip device in a scheme for FRET based imaging.

While the tip (at least its portion 12) undergoes donor excitation that causes energy transfer therein, as schematically showed in FIG. 8A, the FRET interaction leads to donor quenching while inducing acceptor emission (fluorescence), indicating the position of the chromophore with potential for molecular-scale resolution. It should be understood that this process may be achieved by utilizing acceptor-tip and donor-sample as well. It should also be noted that a tip device may be configured with a stem portion and a head portion, wherein the latter actually presents a "tip".

The functionalized tip 10 of the present invention can thus be operable as an excitation source or detector for use in a system for analyzing a sample (generally, "imaging system"). Considering a donor-tip, the tip operates as the excitation source: when the tip is pumped by excitation radiation, it absorbs the exciting energy and can transfer this energy by a dipolar mechanism or by direct emission of a photon thus causing a sample response thereto (acceptor excitation to an excited state followed by acceptor fluorescence). In the case of acceptor-tip, it operates as detector: the tip, when being excited by energy coming from a sample, either directly by absorption or by a dipolar energy transfer mechanism, generates a radiation response indicative of the sample excitation.

Generally, the inventors have developed a technique of preparing novel SPM tips by functionalizing the tips with nanocrystals. Via the binding of the nanocrystals to the tips, the unique photophysical properties of the nanocrystals and their tunability via chemical synthesis are used to create light emitting and/or absorbing scanning probes with controlled emission or absorption, using a single excitation source.

In one particular and non-limiting example, as a first step towards the preparation of the functionalized tips according to the present invention, an appropriate surface chemistry route to link nanocrystals to $Si/SiO_2$ surfaces was pursued using glass substrates as imitating the silicon surface of tips. Organo-silane molecules carrying active end groups such as amine and thiol were reacted either in solution or in gas phase with glass substrates providing silanized substrates having a surface similar to that of oxidized silicon cantilevers, and then imaged with AFM to characterize the quality of the molecular coating. The binding to the nanocrystals was performed by incubating the silanized substrates in nanocrystal solution, preferably at room temperature, although suitable temperatures range from the melting point of the solvent (e.g. for toluene −95° C.), to the boiling point of the solvent (e.g. for toluene 110° C.) After incubation, these substrates were further characterized by AFM, SEM and optical spectroscopy measurements.

Figure 2:
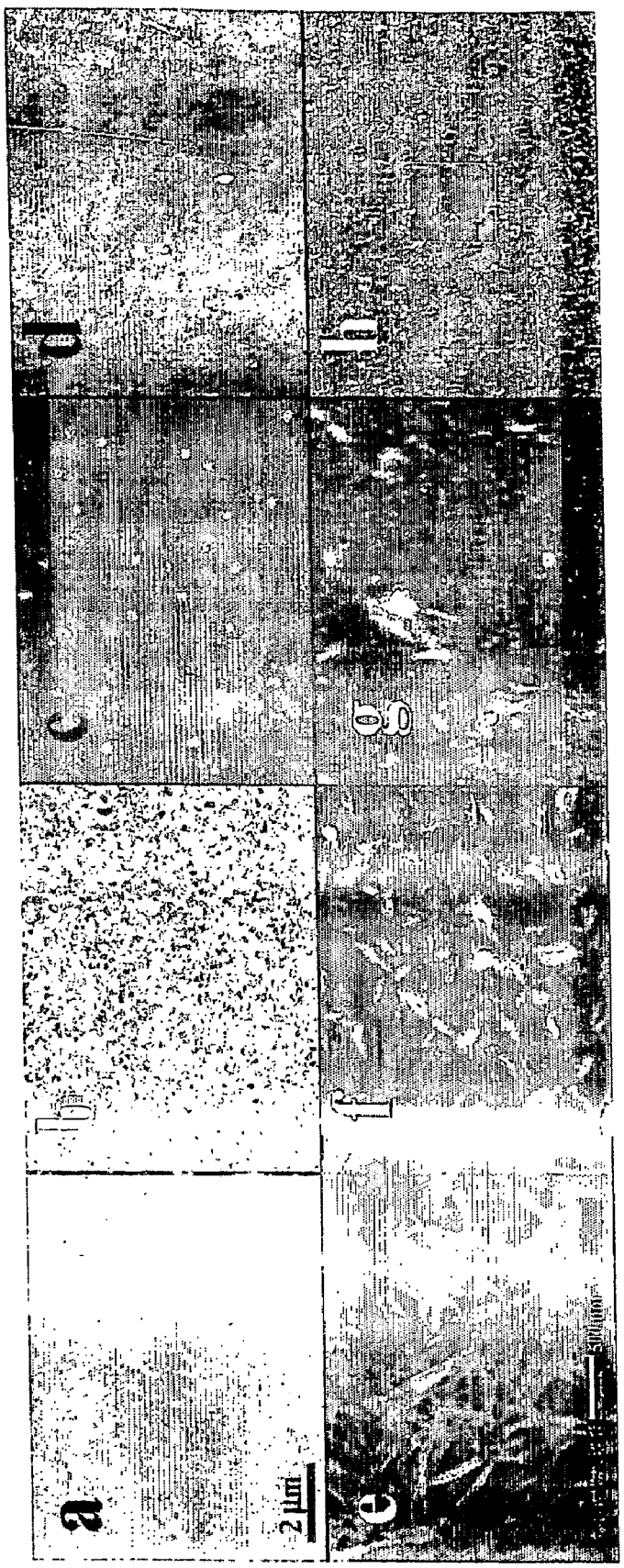
FIG. 2 illustrate AFM images (A-H) of glass substrates after various treatments tested: A—clean glass; B—glass functionalized with APTES in the gas phase, before incubation and F—after incubation in nanocrystal solution; C—glass functionalized with APTES in solution before and G—after incubation incubation; D—glass functionalized with MPTMS in the gas phase before and H—after incubation in nanocrystal solution; and H—a central region of the image emphasized with thin dashed line, shows a 2×2 micron square that was scanned with stronger constant force resulting in dragging of the particles to the scan borders by the tip; E—SEM image of a gas phase APTES functionalized silicon chip. The scale bar in A corresponds to all the AFM images; the height color scale is 10 nm full scale for A,C,D and H; 50 nm for G and 100 nm for B and F.

Silanized surfaces were characterized with AFM in contact mode. FIG. 2 summarizes the AFM characterization of the different coating methods tested on glass coverslips. Soft cantilevers (0.05 N/m) were used while applying minimal force. An attempt to use stiffer cantilevers resulted in damage to the organic layer while tapping mode AFM measurements resulted in anomalous height data and contrast reversal due to the force effect on the resonance frequency. The glass surface before silanization (FIG. 2A) is clean and smooth with a mean roughness of 0.45 nm. The gas phase APTES (aminopropyl-triethoxysilane) treated cover slip shown in FIG. 2B exhibits a rough surface with closely packed polymerized aggregates ranging between 30 to 90 nm in height. SEM imaging of similarly treated silicon surface revealed rodlike polymerization as seen in FIG. 2E. Amine-terminated silanes tend to polymerize and the polymerization is somewhat reduced using solution phase linking.

FIG. 2C shows the surface after treatment with APTES in solution. Evenly distributed silane aggregates are seen, with heights ranging from 5 to 10 nm and average density of about 2 aggregates per square microns. A considerably improved surface was obtained for the gas phase MPTMS (mercaptopropyltrimethoxysilane) treated glass. The roughness of the mercapto-silane functionalized surface is in the order of 0.3 nm and shows only occasional aggregation.

Substrates treated similarly to those discussed above were characterized with AFM after incubation in similar nanocrystal solutions (in this case a $10^{-6}$ M solution of 4 nm CdSe/ZnS dots was used). The bare glass surface showed only occasional large aggregates that were not washed away. Isolated small particles were not detected. In contrast to the bare glass, the silanized substrates show extensive binding of nanocrystals on all the surfaces. The MPTMS treated glass (FIG. 2H) exhibited uniform coverage of nanocrystals with no aggregation while the gas phase APTES treated glass (FIG. 2F) exhibited nanocrystal aggregates. In FIG. 2H, a stronger lateral force was applied by the tip in the central 2 micron region resulting in detaching of bound particles and dragging by the tip to the borders of the scanned area. Fluorescence measurements of the samples, excited at 514 nm, showed photoluminescence (PL) that is similar on all substrates, and closely matches the PL of the same nanocrystals in solution.

From the results of these silanization experiments, it is evident that the gas phase deposition of MPTMS provides some advantages for tip coating over other reagents. This method is easy to implement and yields high quality surface morphology. Minimum exposure to air and water should be exercised after silanization to avoid end group oxidation and contamination. The high affinity of the mercapto end group to the nanocrystal surface, results in high nanocrystal coverage after several hours, e.g. between 2 and 4 hours of incubation in the nanocrystal solution. No effects on nanocrystal emission were observed. Using this coating method, AFM tips emitting various colors were prepared according to desired applications.

Figure 3:
FIG. 3 illustrates HRSEM (High Resolution Scanning Electron Microscopy) images of a MPTMS- nanorod functionalized tip, where 3A—general view, 3B—close up on the tip apex; 3C—close up on tip surface; 3D—close up on cantilever.

Direct characterization of the functionalized tips was performed by HRSEM imaging. FIG. 3 shows HRSEM images of a functionalized AFM tip treated with MPTMS and coated with nanocrystals. For imaging purposes, this tip was functionalized with nanorods 4 nm in diameter and 22 nm long. It is clearly seen in FIG. 3A and FIG. 3B that the tip retains its general features and sharpness. Nanorods were identified on the tip surface, including the tip apex but could be clearly resolved covering the tip surface and most clearly on the tip cantilever which has the best contact to the conducting tape and therefore minimal charging problems (see FIG. 3C and FIG. 3D respectively). Functionalization of the tip surface was therefore successfully implemented and nicely controlled where aggregation could be avoided. It is also noted that the density of the nanocrystals coating the tip could be controlled by modifying the incubation time and concentration of the nanocrystal solution.

Figure 4:
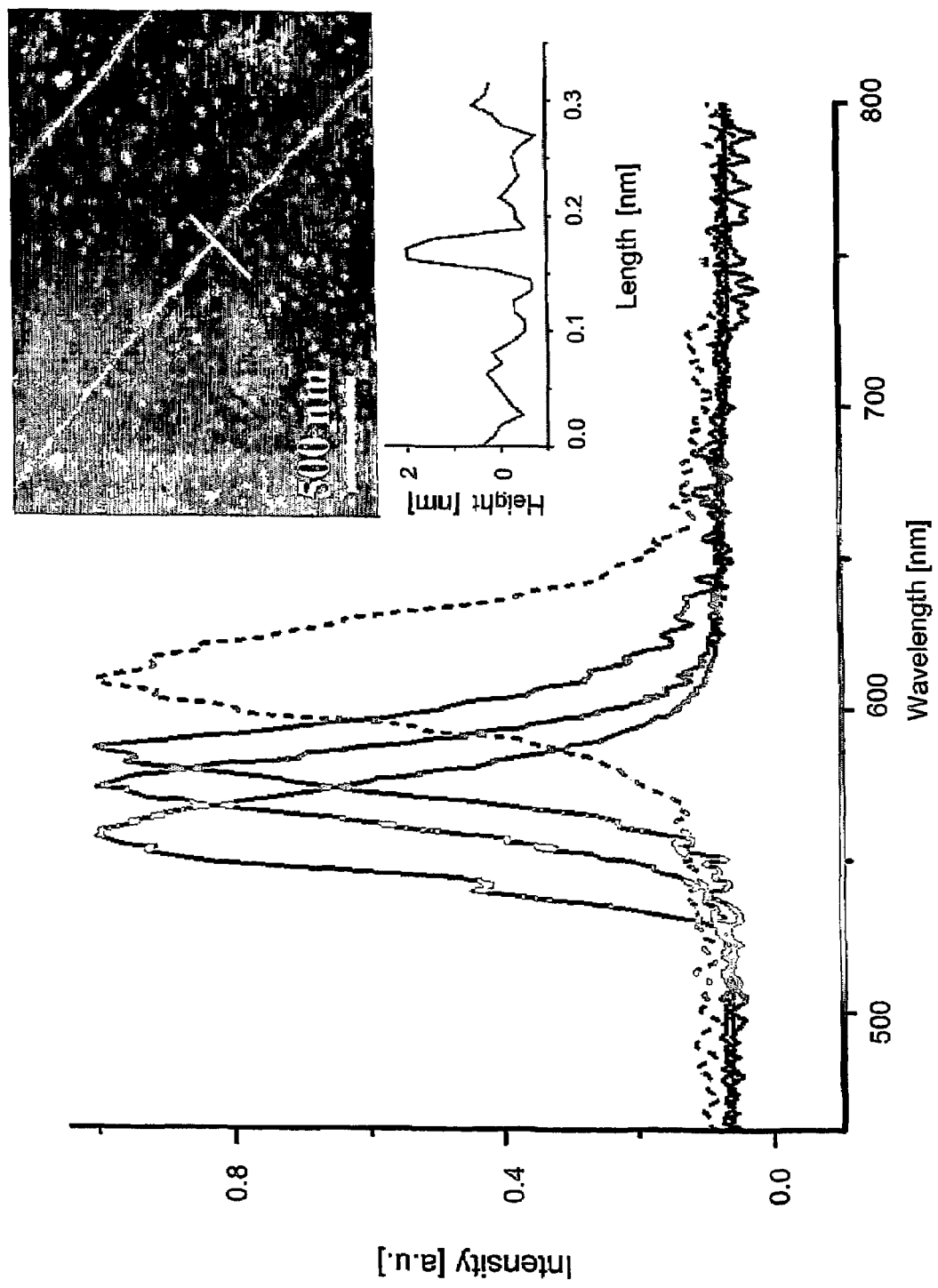
FIG. 4—illustrates emission spectra of four functionalized tips ranging from 556 to 609 mm; from left to right, functionalized with CdSe/ZnS nanocrystals of 3.5, 4 and 4.5 nm in diameter; dashed line spectrum corresponds to the 22×4 nm rods on the tip imaged by HRSEM in FIG. 3.; Inset—AFM image and line section of stretched DNA on glass acquired by the tip emitting at 556 nm.

The emission spectrum from the same tip discussed above was measured with the fluorescence microscope setup and is traced in a dashed line in FIG. 4. The fluorescence was similar to that observed in solution for the same sample. To demonstrate the general applicability of this approach for functionalizing AFM tips with nanoparticles, the inventors performed similar linking experiments for other nanoparticles. Fluorescence from three tips coated with nanocrystals of different sizes is also presented in FIG. 4. The emission color from the tip is easily controlled by depositing nanocrystals of different sizes and in this case, emission spans the range from 556 nm for 3.5 nm CdSe/ZnS dots to 609 nm for 4.5×22 nm rods. The emission range of the functionalized tips could easily be extended to cover a broad range of wavelengths by connecting nanocrystals of other semiconductors from the wide variety of such samples that is presently available. Since the surface chemistry of II-VI, III-V and IV-VI semiconductor nanocrystals is similar, the same functionalization scheme could be used providing tips with emission from the blue to the near infra red (NIR). Metal nanocrystals, for example gold or silver, could be linked in similar fashion for microscopy schemes such as surface enhanced Raman microscopy. In this case of Raman imaging, the nanoparticles on the tip serve as enhancement centers for the Raman process.

An additional important issue for the functionalization process is that it should not hamper the performance of the AFM tip in topographic imaging. This was tested by imaging stretched DNA on glass with the tip emitting at 556 nm as shown in the top left insert of FIG. 4. A cross section of the DNA image reveals a width at half maximum of 26 nm, similar to that achieved with an untreated tip and indicating that the tip remains sharp and capable of high resolution AFM imaging.

FRET Processes Observed on the Functionalized Tip

For FRET microscopy, means for avoiding collection of dye molecules by the tips were required. Such means include for example strong binding of the acceptor molecules to the scanned surface. Nevertheless, in cases where such collection took place, the inventors employed an experimental scheme that involves collecting acceptor dye molecules on the tip apex and then imaging a projection of the tip by scanning it over a diffraction limited excitation spot and collecting its emission. The FRET process in this case was seen to occur on the tip itself, at positions where the dye molecules were collected on the nanocrystal functionalized tip.

Figures 5A, 5B:
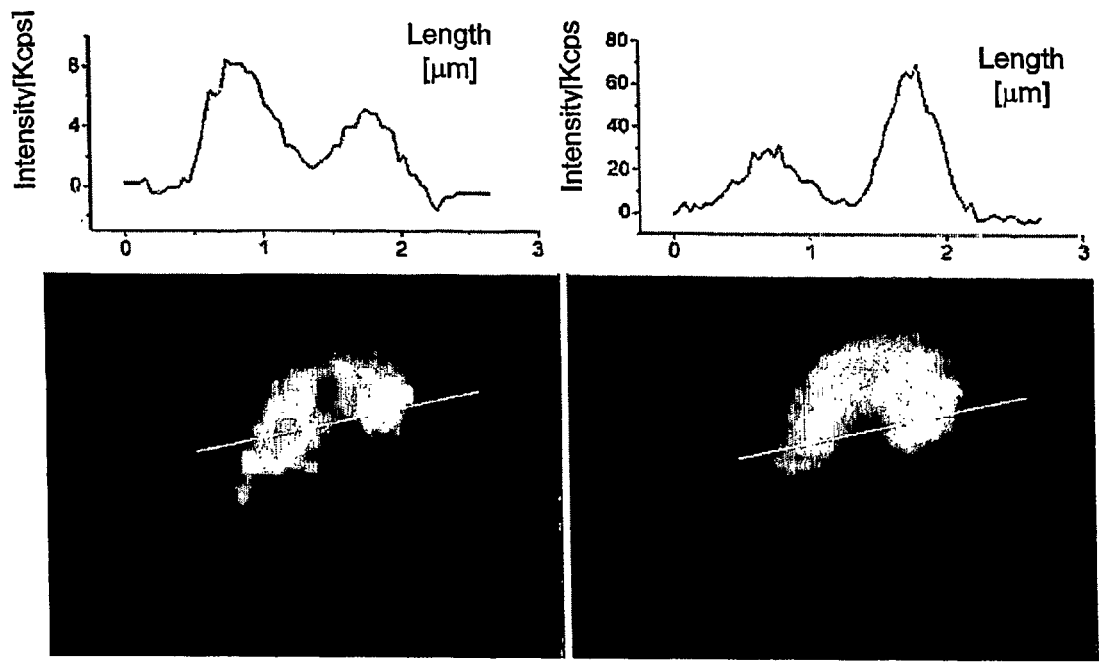
FIG. 5—illustrates local FRET between nanocrystals on the functionalized tip and dye molecules; 5A—fluorescence image of the tip acquired in the acceptor channel and its line section showing dominant acceptor signal intensity on the left region; 5B—fluorescence image of the tip acquired in the donor channel and its line section showing dominant donor signal intensity on the right region; 5C—super imposed image of the tip representing spatially localized donor and acceptor emission from the tip; 5D—spectra taken from: a single dye molecule on the surface emitting at 610 nm.
Figures 5C, 5D:
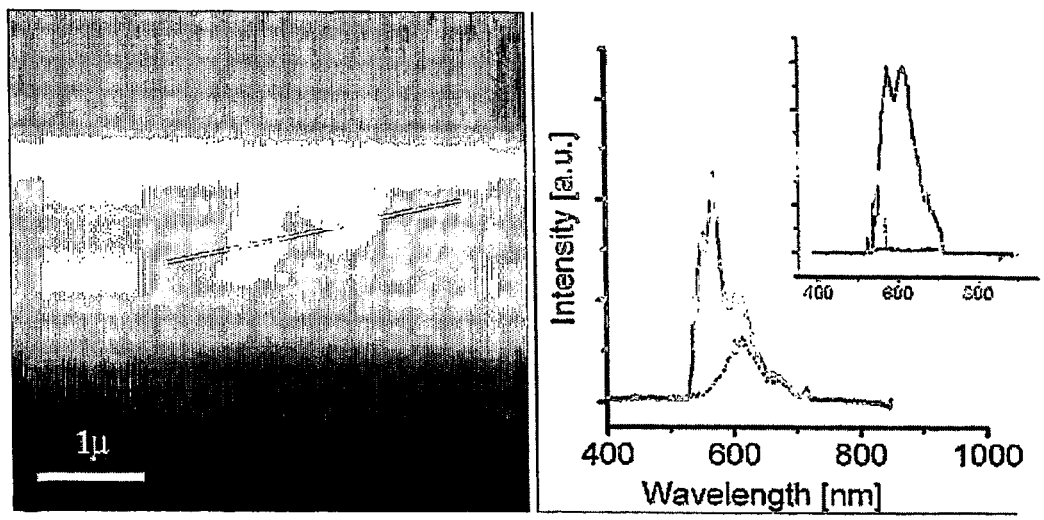

For these FRET measurements, the collected emission was split to two APD (avalanche photodiode) detectors using a 610 mm dichroic mirror. With this setup, donor (nanocrystal) and acceptor (dye) fluorescence was detected nearly independently. A dilute ethanolic solution of Atto-590 (Sigma) dye was spin cast on a clean glass coverslip resulting in separated single acceptor dye molecules. A tip functionalized with 4.5 nm diameter CdSe/ZnS nanocrystals emitting at 570 nm was scanned over the glass surface, raster scanning an area containing approximately 10 dye molecules. In the scanning process, a few dye molecules stick to the tip apex in close proximity to one or more of the nanocrystal donors attached to the tip, thus creating a FRET pair. At this stage, the tip was scanned over the excitation spot while collecting its fluorescence pixel by pixel to create simultaneously the images in FIGS. 5A and 5E, in the two APD's. Such a scan does not provide a microscopic image of the substrate, but rather of the tip itself. The inherent resolution is limited by the size of the laser spot in this case and does not fully manifest the potential high resolution of FRET microscopy. The image in FIG. 5B, collected in the donor channel, represents mainly nanocrystal emission. It can be seen that the emitting area is approximately "n" shaped with a size of about 1.5×1 microns and consists of a bright right lobe and a weaker left region. This reflects the contour of the tip apex. The relative intensities are shown in the line section above the image. FIG. 5A, collected in the acceptor channel, represents acceptor dye emission together with the nanocrystal emission tail. Here, the strongest signal is showed up on the left side and correlates spatially to the weaker part in the donor image. This can be clearly seen if the two images are superimposed as shown in FIG. 5C. Here, the light grey color represents donor emission while dark grey represents acceptor emission, indicating that during scanning acceptor dye molecules have been collected at a specific region of the tip.

The scans in FIGS. 5A-5B show FRET between the nanocrystals and the dye molecules on the tip apex itself, leading to enhanced dye emission along with quenching of the nanocrystal emission. This observation was verified spectrally by taking localized spectra from different regions of the tip, and from isolated dye molecules on the surface. FIG. 5D demonstrates this FRET interaction; the dashed spectrum, taken from the right tip region, is clearly dominated by the donor nanocrystal emission peak centered at 574 nm. The spectrum in solid line was taken from the region with maximum emission in the acceptor channel and both donor and acceptor contributions are seen. The dotted line is a spectrum of a single dye molecule peaking at 610 nm and recorded with higher excitation power due to the low direct excitation by the 458 nm laser line.

The distribution of dye molecules on the substrate is 0-1 molecules per square micron, therefore only a few dye molecules could have been collected by the tip on the scanned area. Furthermore, judging from the density of attached nanocrystals studied previously, only a few particles attached to the apex area can contribute to the FRET interaction. This, together with the observed simultaneous enhancement and quenching of the acceptor and donor emission respectively, indicates that localized FRET interaction is observed to take place on the tip. Disengaging the tip from the surface, results in disappearance of the FRET signal, verifying that this interaction is indeed occurring on the tip surface. The inset in FIG. 5D shows another case where a functionalized tip collected dye molecules from the sample surface during scanning. The solid and dashed lines are spectra of the tip while engaged and disengaged from the surface respectively.

The experiments performed demonstrate that the strong distance dependence of FRET interaction together with tip geometry serves to confine the active photonic volume for FRET to the tip apex. Clearly, the functionalized tips emit light with a micron scale area reflecting their contour within the excitation spot; yet, the FRET signal observed, is localized in an area equivalent to the excitation spot size with a diameter of approximately 400 nm. The fact that in this experiment all FRET signals come from the tip, which is scanned over the excitation spot, limits the resolution to the diffraction-limited spot size. Nevertheless, for surface immobilized acceptors, resolution is significantly improved by over one order of magnitude.

"Negative" FRET Imaging:

Silicon AFM tips were functionalized with InAs nanocrystals. These nanocrystals absorb radiation from the near IR region (1300 nm) all across the visible and UV and therefore act as acceptors for any FRET interaction with visible light emitting chromophores. In an illustrative experiment, CdSe nanocrystals emitting at 570 nm were embedded in a thin (5-10 nm) layer of PMMA on a glass substrate to serve as FRET donors.

Figure 6:
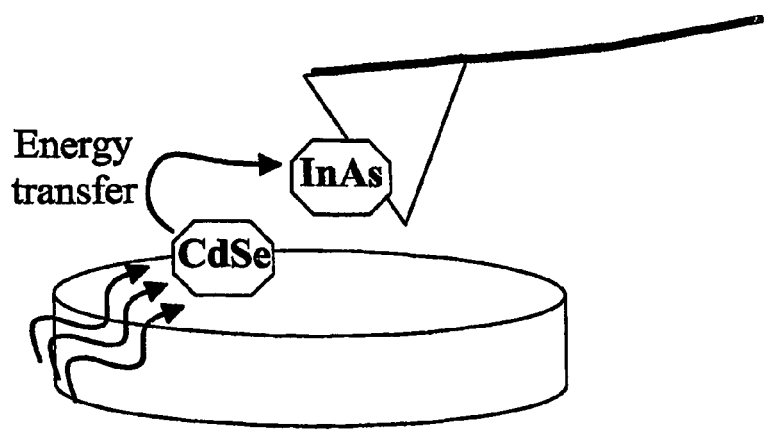
FIG. 6—schematic illustration of FRET from CdSe nanocrystals as donors on the surface, to InAs nanocrystals as acceptors bound to the scanning AFM tip.

The emission from single particles was detected continuously while the fuctionalized tip scans the region around the detected nanocrystal. As the tip passes over the nanocrystal, the excited state energy is transferred non-radiatively to the InAs acting as acceptor particles on the tip, as schematically showed in FIG. 6. The result of this process is the local darkening of the detected CdSe nanocrystal. The image created by the full raster scan of the tip over the examined region consists of a dark spot representing the location of the donor CdSe particle. These dark spots have a width at half max of 25-45 nm, as may be observed in FIGS. 7A and 7B, showing fluorescence quenching for the InAs functionalized tip, over a CdSe nanocrystal. The dark spots are the region where the proximity of the acceptor functionalized tips to the CdSe donor has led to quenching due to FRET. When the tip is not on top of the nanocrystal, regular far field emission is detected, which shows dark streaks due to the well known on-off blinking present for semiconductor nanocrystals. Control experiments using bare Silicon tips that were not functionalized with nanocrystals show no quenching of the emission.

The resolution of about 25 nm achieved in the above experiment represents an order of magnitude improvement over the far-field resolution limit of about 300 nm and directly demonstrates the use of nanocrystal-functionalized tips of the invention for high resolution nanometer scale optical imaging.

EXPERIMENTAL

CdSe/ZnS core/shell nanocrystals and nanorods were prepared by known methods of colloidal nanocrystal synthesis utilizing high temperature pyrolysis of organometallic precursors in coordinating solvents [11, 12, 13, 14, 15]. Glass cover slips were sonicated in detergent solution for 15 minutes, thoroughly washed in distilled water and baked in an oven for 5 hours at 500° C. yielding highly hydrophilic, optically clean glass. Silicon substrates and silicon AFM tips (mikromasch NSC11 and CSC12) were activated for 20 seconds in concentrated nitric acid to yield a clean, hydroxyl rich surface.

The surface of the substrates and the tips were silanized using aminopropyltriethoxysilane (APTES) (Aldrich) or mercaptopropyltrimethoxy-silane (MPTMS) (Fluka), either in solution or in the gas phase.

Gas phase silanization of the mercapto and amine terminated silanes was performed as follows: glass coverslips were placed on a Teflon holder inside a glass jar containing a few drops of organo-silane. The jar was sealed, heated to 70° C., and the coverslips were left to react overnight with the silane vapor.

Silanization in solution was performed in a 2% (v/v) organo-silane ethanolic mixture where 5% high purity water was added. The mixture was left to hydrolyze for 5 minutes after which the glass coverslips were introduced into solution for an additional 2 minutes. In the case of MPTMS, rapid polymerization occurred upon addition of water to the mixture as could be seen by the formation of a white polymer-like solid.

After silanization, samples were washed with ethanol (Aldrich), dried with a flow of nitrogen and incubated for 3 to 6 hours in a 10-6 M solution of nanocrystals in toluene (Aldrich). After incubation, the samples were washed with toluene to remove unbound particles, dried with nitrogen flow and stored in the dark under inert conditions until characterized. Dye stained λ-DNA (NEB-λ-DNA, molecular probes-BOBO-3) and dispersed dye molecules (Texas red, BODIPY TR-X-molecular probes & ATTO 590-sigma) were used as test-acceptor chromophores.

For HRSEM imaging of the tips, the cantilever was broken off the silicon chip and mounted directly on double sided carbon tape to minimize charging effects. Measurements were performed on a FEI-Sirion HRSEM with a field emission gun source using voltages of 2-10 kV.

Figure 8B:
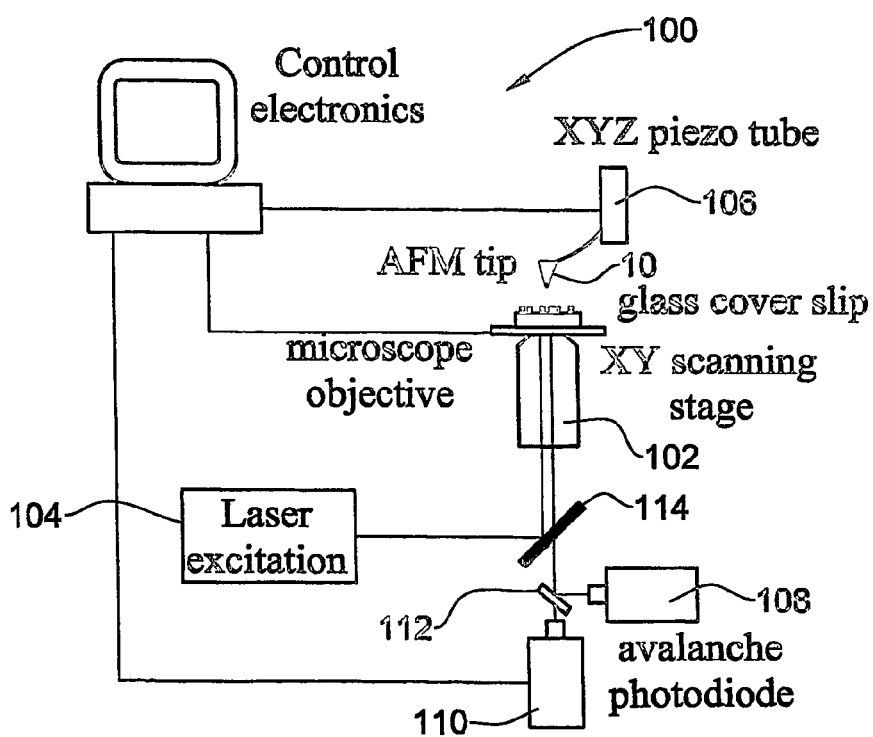
FIG. 8B—is a schematic representation for the experimental system for correlated AFM and optical measurements.

AFM and optical measurements were performed using a system for correlated AFM and scanning fluorescence microscopy, as schematically illustrated in FIG. 8 and generally designated 100. Briefly, an AFM head (Digital instruments-bioscope) is mounted on an inverted microscope (Zeiss-axiovert 100) equipped with a 100×, 1.4 NA oil immersion objective (Zeiss) 102. The 458 nm line of an argon ion laser 104 (Melles gliot-LAP 321) is focused to a tight spot on the sample surface, and excites the sample in an epi-illumination configuration. This is implemented using a tip 10 according to the invention (namely, having at least a distal portion thereof (top portion of the conically shaped tip) formed with an active medium in the form of nanoparticles). Fluorescence is collected by the same objective lens 102 and directed along an imaging channel to a LN2 cooled CCD spectrograph 108 (Princeton Instruments-LN-CCD1100, Acton-SP150) and/or along a measurement channel to a dualcolor avalanche photodiode (APD) arrangement 110 (Perkin Elmer-spcm-14) for separate detection of donor and acceptor emission. If the use of both imaging and measuring channels is considered, the collected fluorescence is appropriately separated by a light separating assembly 112 (such as splitter or pinhole) into two spatially separated light components propagating to detectors 108 and 110, respectively. A beam splitter 114 separates the excited radiation coming from the laser source and the collected fluorescence. For correlated topography and fluorescence measurements, the AFM tip is positioned within the diffraction limited excitation spot and the sample is raster scanned by a separate piezo scanning stage 106 (Nanonics-flatscan). This allows for simultaneous recording of the fluorescence and the topography of the sample, and at the same time provides an ideal setup for apertureless NSOM studies. In the present experiments, the tip was scanned over the diffraction limited laser spot. This provides means for microscopic characterization of the fluorescence from the tip with resolution that is limited by the spot size (about 0.5 micron), as described above.

It should be understood that although the inverted microscope configuration and excitation through a transparent substrate is described here, the tip device of the present invention may be used in any other configuration of an imaging system. For example, it is possible to use the tips with an opaque sample with an upright-microscope, in which case the excitation and light collecting channels are located at the same side. Yet another possible configuration employs a mirror to collect light from the tip region.

Those skilled in the art will readily appreciate that various modifications and changes can be applied to the embodiments of the invention as hereinbefore described without departing from its scope define in and by the appended claims.

The invention claimed is:

1. A tip device having at least a portion thereof comprising a substrate layer functionalized by nanoparticles comprising nanocrystals which are bound to a surface of said substrate,
the nanocrystals acting as active media capable of interacting with a predetermined sample to form with the sample a donor-acceptor or acceptor-donor pair,
said interaction of the tip with the sample modifying light emission of the sample by transferring or accepting energy to or from the sample.

2. The device according to claim 1, wherein said substrate is made of at least one of the following materials: insulator-, semiconductor-, and conductor-based material.

3. The device according to claim 1, wherein the nanoparticles form a structure comprising one or more layers comprising at least one sub-monolayer, or monolayer.

4. The device of claim 3, wherein the nanoparticles are bound to said surface either directly or through a linker molecule.

5. The device according to claim 1, wherein the nanocrystals are made of one or more semiconductor, metal or oxide materials.

6. The device according to claim 5, wherein said nanocrystals comprise one or more nanocrystals having at least one of the following shapes: spherical, nearly spherical, rod, branched shape, wire, and tube.

7. The device according to claim 5, wherein said nanoparticles are made of nanocrystal material comprising at least one of the following: CdSe/ZnS, InAs, InP, GaP, GaAs, InSb, GaSb, GaN, Si, Ge, CdTe, CdSe, ZnSe, ZnO, Au, Ag, Pt, Ni, Pd, In, and Bi.

8. A method of forming a tip device for us in analyzing a sample, the method comprising reacting a surface of at least a portion of the tip with nanoparticles comprising nanocrystals in solution, powder or film so as to bind said nanoparticles to said surface thereby functionalizing said surface by said nanoparticles capable of acting as active media interacting with a predetermined sample to form with the sample a donor-acceptor or acceptor-donor pair,
said interaction of the tip with the sample modifying the light emission of the sample by transferring or receiving energy to or from the sample, respectively.

9. The method according to claim 8, wherein said surface of the tip is made of or coated by at least one of the following materials: Si, Au, Ag, Pt, Ti, Co, Cr, Ir, $Si_3N_4$, TiN, glass, diamond and carbon.

10. The method according to claim 8, wherein said surface of said at least portion of the tip is made of at least one of the following materials: insulator-, semiconductor- and conductor-based material.

11. The method according to claim 8, wherein the nanoparticles form a structure comprising one or more layers comprising at least one sub-monolayer or monolayer.

12. The method of claim 8, comprising reacting said surface within said at least portion of the tip with linker molecules so as to obtain a tip having at least a portion thereof bound to the linker molecules, and carrying out said reacting of said at least portion of the so-obtained tip with the nanoparticles solution, powder or film.

13. The method according to claim 12, wherein said linker molecules are organic molecules bearing at least two functional groups, one of the functional groups being capable to react and bind to the surface and another of the functional groups being capable to react and bind to the nanoparticles.

14. The method according to claim 12, comprising:
providing the tip device with said surface within at least portion of the tip being made from at least one of the following materials: Si, $SiO_2$, glass, titanium oxide, TiN or $Si_3N_4$;
silanizing said surface with an organosilane compound either in solution or in gas phase; and
exposing the silanized portion to a solution, powder or film comprising the nanoparticles.

15. An optical apparatus for the use in analyzing a sample, the apparatus comprising at least one tip device configured according to claim 1.

16. The apparatus according to claim 15, comprising a light source assembly, which comprises a pumping source operable to generate excitation radiation and said at least one tip device, which when pumped emits exciting energy to irradiate a sample and thus cause a radiation response of the sample.

17. The apparatus according to claim 15, comprising a light source assembly, which comprises a pumping source and said at least one tip device, the tip device when pumped by exciting radiation absorbs the exciting energy and transfers this energy, by a dipolar mechanism or by direct emission of a photon, to irradiate a sample and thus cause a sample response thereto.

18. The apparatus according to claim 15, comprising a light source assembly and detection assembly, the detection assembly comprising said at least one tip device, which when excited by energy coming from a sample, generates a radiation response indicative of the sample excitation.

19. The apparatus according to claim 15, comprising a light source assembly and a detection assembly, the detection assembly comprising said at least one tip device, the tip device, when being excited by energy coming from a sample, either directly by absorption or by a dipolar energy transfer mechanism, generates a radiation response indicative of the sample excitation.

20. The apparatus of claim 15, configured and operable as a fluorescent Resonance Energy Transfer (FRET)-based microscope.

21. The apparatus of claim 15, configured and operable as a light source.

22. The apparatus of claim 15, configured and operable as a Raman microscope, said nanoparticles serving to locally enhance a Raman signal.

23. The apparatus of claim 15, configured and operable as a second harmonic generation microscope, said nanoparticles serving to locally enhance a second harmonic signal.

24. The apparatus of claim 15, configured and operable as a non-linear optical microscope with the nanoparticles serving to locally enhance a signal.

25. The apparatus of claim 15, configured and operable as a scanning probe microscope for topography imaging.

26. The apparatus of claim 15, configured and operable as a chemical force microscope.

27. A method for use in imaging a sample, the method comprising causing an energy interaction in a donor-acceptor pair formed by the tip of claim 1 and the sample, and detecting a radiation response to said interaction indicative of sample characteristics.

28. The method of claim 27, wherein the radiation response includes radiation generated in the sample in response to exciting energy coming from the tip.

29. The method according of claim 27, wherein the radiation response includes radiation generated by the tip in response to exciting energy coming from the sample.

30. The method according to claim 8, wherein said binding of the nanocrystals comprises incubating the substrate in a solution containing nanocrystals at substantially room temperature.

31. The method according to claim 30, wherein said substrate is silanized before said incubating.

32. The method according to claim 30, wherein the temperature of incubation is in a range from a melting point of a solvent to a boiling point of said solvent.

33. The method according to claim 32, wherein the solvent is toluene, the melting and boiling points being 95° C. and 110° C., respectively.

34. The tip according to claim 13, wherein said functional groups include at least one of the following: silane, thiols, carboxylate and amines.

* * * * *